United States Patent [19]

Mills

[11] Patent Number: 4,532,931
[45] Date of Patent: Aug. 6, 1985

[54] PACEMAKER WITH ADAPTIVE SENSING MEANS FOR USE WITH UNIPOLAR OR BIPOLAR LEADS

[75] Inventor: Perry A. Mills, Roseville, Minn.

[73] Assignee: Cardiac Pacemakers, Inc., St. Paul, Minn.

[21] Appl. No.: 626,525

[22] Filed: Jun. 29, 1984

[51] Int. Cl.³ .............................................. A61N 1/36
[52] U.S. Cl. ............................. 128/419 PG; 128/902
[58] Field of Search ......................... 128/419 PG, 902

[56] References Cited

U.S. PATENT DOCUMENTS

| | | | |
|---|---|---|---|
| 3,345,990 | 10/1967 | Berkovits | 128/419 PG |
| 3,735,766 | 5/1973 | Bowers et al. | 128/419 P |
| 4,289,134 | 9/1981 | Bernstein | 128/419 PG |
| 4,301,805 | 11/1981 | Peers-Trevarton et al. | 128/419 P |
| 4,402,322 | 9/1983 | Duggan | 128/419 PG |

Primary Examiner—William E. Kamm
Attorney, Agent, or Firm—Orrin M. Haugen; Thomas J. Nikolai; Douglas L. Tschida

[57] ABSTRACT

A sensing circuit for a cardiac stimulator which can adapt to the use therewith of either bipolar leads or unipolar leads without the need for telemetric programming of a switch internal to the implanted pacemaker. If a unipolar lead is plugged into the terminal receptacle of the pacer at the time of implant, the pacer will sense R-wave activity and other artifacts between a distal tip electrode and the metal body of the pacemaker, but if a bipolar lead is plugged into that same receptacle at the time of implant, the pacer will sense such artifacts between a tip electrode and a ring electrode spaced a predetermined short distance proximally of the tip electrode along the surface of the lead body.

4 Claims, 3 Drawing Figures

PACEMAKER WITH ADAPTIVE SENSING MEANS FOR USE WITH UNIPOLAR OR BIPOLAR LEADS

BACKGROUND OF THE INVENTION

I. Field of the Invention

This invention relates generally to implantable body organ stimulators, and more specifically to a demand-type cardiac pacer whose sensing circuitry is capable of working with either bipolar or unipolar style pacing/sensing leads.

II. Discussion of the Prior Art

Since the late 1950's and early 1960's, considerable progress has been made in the design and manufacture of cardiac pacers. Early models were asynchronous in operation, producing stimulating pulses at regularly spaced intervals over the life of the power supply (batteries) used therein. These pacemakers comprise an electronic pulse generating circuit which is suitably encapsulated so that the device can be totally implanted within the body of the recipient and the stimulating pulses emanating from the pulse generator are coupled to the organ (heart) to be stimulated by way of elongated flexible pacing leads. Basically, two forms of pacing leads have been used—unipolar and bipolar. A unipolar lead commonly comprises an elongated flexible conductor embedded in an insulating body and extending from a distal tip electrode to a male terminal pin located at the proximal end of the lead. This terminal pin is adapted to mate with an appropriate female output jack on the pacemaker. The indifferent electrode for the unipolar pacing system generally comprises a conductive portion on the housing for the pacemaker electronics which is large when compared to the area of the tip electrode. A bipolar lead, on the other hand, generally includes a pair of elongated, flexible, conductive filaments embedded in a suitable insulative material, one of the conductors being connected at its distal end to a tip electrode and the other conductor being connected to a ring or spot electrode disposed on the surface of the insulative body and located a short predetermined distance proximally of the tip electrode. In the bipolar configuration, the proximal ends of the elongated conductors are connected to electrically discrete areas on a male terminal pin which is adapted to mate with the female jack on the pacer itself. A pacer-generated pulse would be applied between the tip and ring electrodes.

Following the development of the asynchronous pacer, so-called demand-type pacers were invented and functioned to inhibit artificial stimulation of the heart in the event that the heart was beating of its own accord. In a demand-type pacer, a sensing means is provided for detecting the occurrence of natural R-wave activity in the body and for resetting a resettable timing means upon the occurrence of such a R-wave. The pulse generator then produces a stimulating output signal only if the resettable timing means is not reset within a prescribed predetermined interval.

Demand-type pacemakers of the type described are also classified as either unipolar or bipolar, depending upon the manner in which pacing and sensing is accomplished. If the sensed R-wave signals are developed between the tip electrode and the metallic body of the pacemaker, sensing is said to be unipolar. Similarly, if the detected R-wave activity is developed between the tip electrode and the proximally located ring electrode, sensing is said to be bipolar.

In that pacemakers can use one of two types of leads, the possibility exists for an implanting physician to mistakenly join a unipolar lead to a pacer which is specifically designed for bipolar operation and vice-versa. This could lead to the implantation of a non-functioning system if the error should go undetected. Perhaps of a greater likelihood is the possibility that one may make a mistake when the pacer is designed to be programmable between the types of leads. The physician may use an external programmer to call for a bipolar lead when, in fact, a unipolar lead has been implanted and vice-versa.

The Bowers et al U.S. Pat. No. 3,735,766 is directed to an early attempt to provide an asynchronous pacemaker capable of operating in either a unipolar or a bipolar mode. The system of the Bowers patent contemplates that when the pacemaker is sold, it will be fully encapsulated within an insulative coating. To achieve bipolar pacing, a two conductor lead would be coupled between the pacer's connector block and the heart. Bipolar pacing will then take place between the two electrode elements disposed near the distal end of the catheter. To achieve unipolar pacing with the device of the Bowers et al patent, a portion of the insulative coating is capable of being readily peeled away from the pacer body, exposing an indifferent electrode area. The indifferent electrode is connected to one side of the pacer's pulse generator while the connector pin of a single-conductor (unipolar) lead mates with the output connection of the pulse generator. The Bowers et al patent is strictly an asynchronous pacer and is incapable of operating in a demand mode. The pacer system is not self-adaptive to the particular type of lead employed and the physician must be sure to join a bipolar lead to the pacemaker when bipolar pacing is to take place and a unipolar lead when unipolar pacing is to take place. In addition, he must remove the insulative covering from the pacer body to expose the indifferent electrode when unipolar pacing is desired.

The Bernstein U.S. Pat. No. 4,289,134 describes a catheter arrangement including built-in electronic circuitry so that when this special-purpose lead is used with a bipolar demand-type cardiac pacer, it converts a bipolar pacing system into a tripolar pacing system in which stimulation is applied between two intra-ventricular electrodes, while sensing of ventricular depolarization is obtained by an alternative pair of electrodes. Thus, when the Bernstein lead arrangement is available, a physician has the option of sensing in either a bipolar fashion between two intra-ventricular electrodes by using a standard bipolar lead, or in a unipolar fashion between one electrode located in the ventricle and the return electrode in the atrium by using the Bernstein lead itself.

The Peers-Trevarton U.S. Pat. No. 4,301,805 describes a connector system usable with either a unipolar lead or a bipolar lead. Whether the pacemaker operates in a bipolar or unipolar fashion depends again upon the particular mechanical connections made by the physician.

Lastly, the Duggan U.S. Pat. No. 4,402,322 describes a pacer system which can function in either a bipolar or a unipolar mode. In the system of the Duggan patent, however, the mode is either fixed during the manufacturing process or, alternatively, may be alterable through programming of the pacer via a telemetry mechanism.

SUMMARY OF THE INVENTION

The goal of the adaptive sensing technique of the present invention is to automatically allow a body organ stimulator, such as a cardiac pacemaker, with no internal changes, to sense R-waves and possibly other body-generative electrical potentials in a unipolar fashion, when a unipolar lead is attached to the pacemaker, and in a bipolar fashion, when a bipolar lead is so attached. In each instance, the electrical stimulation provided by the pacemaker is applied in a unipolar fashion, i.e., between a stimulating tip electrode and the conductive case in which the pacer pulse generator and associated circuitry and power supply is packaged.

The adaptive sensing technique of the present invention is applicable to both single chamber pacers or dual chamber pacers and, in a way, adaptive sensing tends to be more useful in dual chamber pacers because of the possibility of reducing four distinct models to a single unit. The four different models of dual chamber pacers are those that sense electrical artifacts in both the atrium and the ventricle where unipolar sensing is employed in each chamber, where bipolar sensing is employed in each chamber, where unipolar sensing is employed in the atrium with bipolar sensing in the ventricle and finally where bipolar sensing occurs in the atrium and unipolar sensing occurs in the ventricle. Further, in the case of a unipolar/bipolar programmable dual chamber pacer, it is possible to eliminate a significant number of programmable switches when adaptive sensing is employed.

In accordance with the present invention, automatic adaptive sensing is achieved through proper attention to impedance ratios and voltage division at the input terminals of sensing amplifier employed. The cardiac pacing system includes electrical lead means comprising one or more distally disposed electrodes coupled by one or more elongated conductors to a coaxial proximal connector pin. It also includes an implantable pulse generator means having a resettable timing means coupled thereto for causing the pulse generator means to produce electrical stimulating pulses at predetermined intervals unless the timing means is reset prior to the end of said predetermined intervals. The pacer further includes a sensing means which is coupled to the resettable timing means, all of which are housed in a moisture-proof container made, at least in part, from a conductive material which, when said housing is implanted in a living body, is in contact with tissue and body fluids. The container is equipped with terminal means for receiving the coaxial proximal connector pin of the lead means. Further characterizing the invention is the fact that the sense amplifier means exhibits a relatively high input impedance between its pair of input terminals. First and second impedance elements, each internal to the pacer housing and of a value which is relatively high in comparison to the impedance of human tissue and body fluids, but relatively low in comparison to the input impedance of the sensing amplifiers are electrically coupled at one end thereof to the conductive material of the container and individually connected at their other ends to a first and a second of the pair of input terminals of the sense amplifier. A first of the spaced contact in the pacer's terminal means is joined to the first input terminal of the sense amplifier and, likewise, the second spaced contact of the pacer's terminal means is joined to the second input terminal of the sense amplifier. When the coaxial proximal connector pin of either a unipolar or a bipolar lead is inserted into the pacer's terminal means, the first and second spaced contacts therein mate with the appropriate contact(s) on the connector pin of the lead employed.

Using this arrangement, when a unipolar lead is coupled to the terminal means of the pacer, one input of the sensing amplifier is controlled by the conductive portion of the pacemaker container through one of the two impedance elements and the second input to the sense amplifier is controlled directly by the tip electrode. When a bipolar lead is used, one input of the sensing amplifier is still controlled directly by the tip electrode on the lead but the other input is controlled by the somewhat proximally displaced ring or surface electrode instead of the metal portion of the pacer's container in that the tissue and body fluid impedance between the tip electrode and the ring or surface electrode is much lower than the ohmic value of the impedance elements employed.

The sensing mode thus automatically adapts to the particular type of lead which is joined to the pacer. This obviates the possibility of a physician erring in making hardware connections or in programming the sensing function in a programmable unit.

OBJECTS

Accordingly, it is a principal object of the present invention to provide an improved sensing means for a demand-type pacemaker which is automatically adaptive to the particular style of lead used with the pacemaker. Another object of the invention is to provide a self-adaptive pacemaker which can employ either unipolar leads or bipolar leads without the need for reprogramming.

Still another object of the invention is to provide in a demand-type pacemaker a sensing arrangement which is independent of the type of lead (unipolar or bipolar) used to couple the pacemaker to the patient's heart.

These and other objects and advantages of the invention will become apparent to those skilled in the art from the following detailed description of a preferred embodiment, especially when considered in conjunction with the accompanying drawings in which like numerals in the several views refer to corresponding parts.

DESCRIPTION OF THE PREFERRED EMBODIMENT

Figure 1:
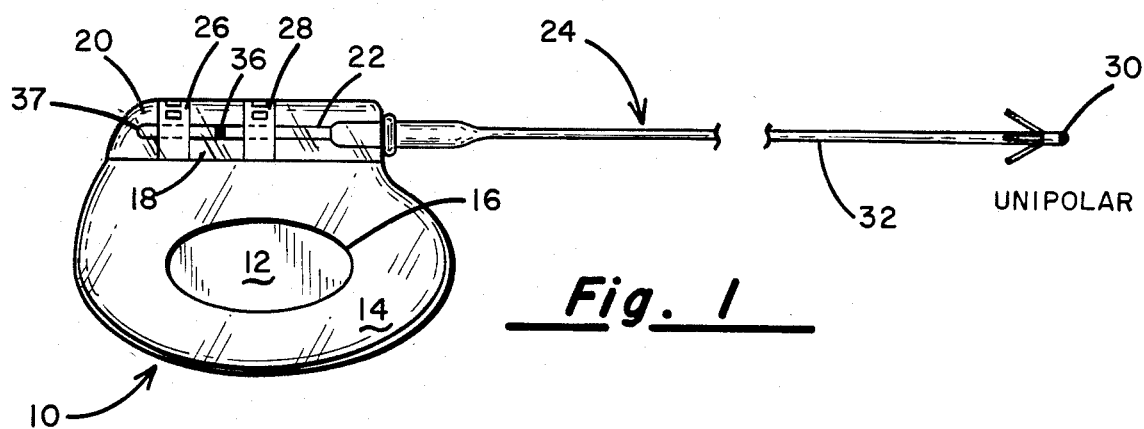
FIG. 1 is a side elevation view of an organ stimulator equipped with a unipolar lead.

Referring to FIG. 1, there is illustrated an electrical stimulation device for applying stimulating signals to a body organ. Specifically, there is identified, generally by numeral 10, a programmable unipolar/bipolar cardiac pacemaker, and it is seen to include a housing or container 12 which is moisture-proof and generally inert to body fluids. The container is preferably fabricated from titanium or other suitable metal and is covered over a majority of its surface area by a insulative plastic coating 14. The coating is absent in the zone defined by the oval window 16 and, thus, the metallic conductive material of the container is exposed through that window. This exposed metallic surface functions as an indifferent electrode when unipolar pacing is involved.

Suitably affixed to the top surface 18 of the plastic-coated container 12 is an epoxy header 20 which is sealed to the pacemaker's can and which defines a female receptacle into which the proximal male connector pin 22 of a pacer lead assembly 24 may be inserted. Embedded within the epoxy header 20 are first and second terminals 26 and 28 which feed through appropriate seals into the container 12 so as to make electrical contact with the electronic circuitry contained therein. The pin 22 of the lead is arranged to pass through aligned apertures in the terminal posts 26 and 28 and set screws may be fitted into threaded openings in the header 20 from the top so as to tighten down upon the cylindrical surfaces of the pin 22 holding the pin firmly in contact with the terminal posts for good electrical connection.

The lead 24 in FIG. 1 is of conventional design for a unipolar lead and includes an elongated conductor (not shown) extending from the male pin 22 at the proximal end of the lead down to a metallic tip electrode 30 at the extreme distal end of the lead. The elongated conductor is embedded in a flexible plastic sheath 32. The terminal pin 22 is of a coaxial design with the segments 22 and 37 being electrically isolated from one another by insulator 36.

In the case of a unipolar lead, only the terminal post 28 needs to make electrical contact with the terminal pin segment 22. Terminal post 28 is connected internally of the pacemaker to the output from the pulse generating circuitry. In that segment 37 of the coaxial terminal pin is designed to be electrically insulated from segment 22 thereof when the male pin is fully inserted into the female receptacle, only segment 22 will electrically engage the terminal post 28 coupled to the output of the pulse generator. In a unipolar lead, there are no conductive elements coupled to the terminal pin segment 37.

Figure 2:
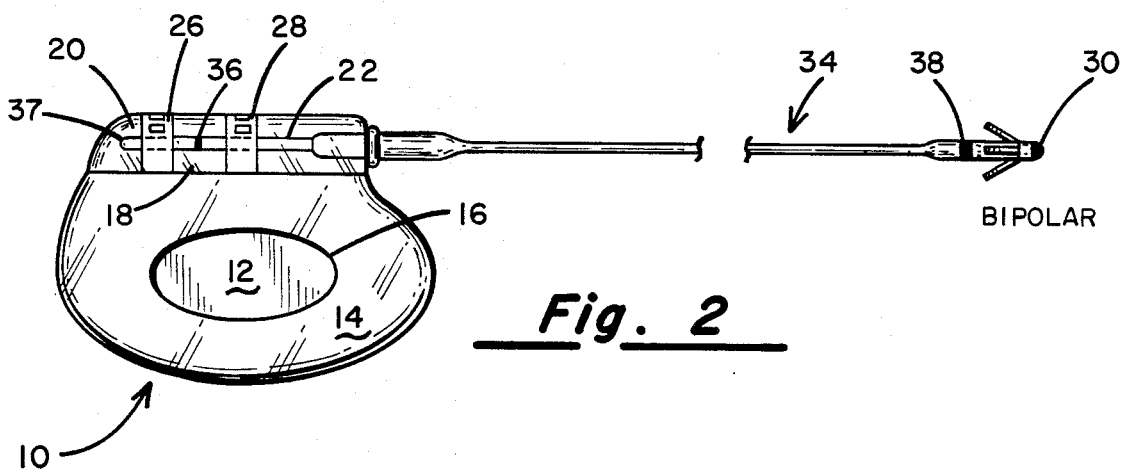
FIG. 2 is a side elevation view of an organ stimulator equipped with a bipolar lead.

With reference to FIG. 2, the organ stimulator 10, which again may be a demand-type cardiac pacemaker, is identical in its construction to the pacemaker shown in FIG. 1 but the style of pacer lead used therewith is different. Specifically, a bipolar lead, indicated generally by numeral 34, is shown and includes a proximal male connector pin 22 of a coaxial design in which respective separate segments of the terminal pin are electrically isolated from one another as by a suitable insulator 36. Two flexible conductors (not shown) extend from the terminal pin segments the length of the catheter lead, one conductor being connected to the tip or stimulating electrode 30 and the other being electrically connected to the bipolar ring or surface electrode 38, which is disposed a short predetermined distance proximally of the tip electrode 30. In this fashion, the tip electrode 30 is electrically connected only to the terminal post 28 while the ring or surface electrode 38 is electrically connected only to the terminal post 26 of the pacer.

With the foregoing understanding of the physical construction of the pacemaker in mind, consideration will next be given to the schematic diagram in FIG. 3 where it wil be explained how the sensing amplifier can be considered self-adaptive to the particular style of lead (unipolar or bipolar) used with the pacemaker. In that the present invention may find use with a variety of organ stimulators, and because such organ stimulators are well known in the art, it is not deemed necessary for a full teaching of the invention to set out the specific electronic circuitry employed. Instead, the major portions of the organ stimulator are reflected by a block diagram and are shown to include a pulse generator 40 which, in its simplest form, may comprise a semiconductor switch in circuit with an energy source and connected between the indifferent electrode (the metal container 12 for the circuitry exposed through the opening 16) and the pacer's output terminal 42. The semiconductor switch (not shown) is arranged to be controlled by a resettable timing means 44 of a known design in which the pulse generator wil be enabled to issue an output stimulating signal, provided a predetermined time elapses during which the timing means 44 is not reset. The resettable timing means, in turn, is controlled by the output from a suitable sense amplifier 46. This sense amplifier "listens" for electrical activity in the body, e.g., R-waves resulting from ventricular depolarization, and if the signal applied to the sense amplifier via the lead employed exceeds a predetermined threshold, the timing means 44 will be reset to block or inhibit the generation of a stimulating pulse.

The sense amplifier 46 is specifically designed to present a relatively high input impedance $R_{in}$ to its input terminals 48 and 50. The input terminal 48 is coupled through a coupling capacitor 49, the terminal post 28 and male pin 22 of the lead to the tip electrode 30 of either the bipolar or the unipolar lead. The input terminal 50 of the sense amplifier is coupled through the terminal post 26 and the portion of the male coaxial pin connector 37 to the bipolar ring electrode 38.

Internal to the pacemaker, there is also provided a first impedance element $R_1$, which is connected between the sense amplifier input terminal 50 and the indifferent electrode, i.e., the pacemaker container. Similarly, an impedance element $R_2$ is connected between the sense amplifier input terminal 48 and that indifferent electrode. The impedance values of the elements $R_1$ and $R_2$ are such that they are relatively low in comparison to the input impedance $R_{in}$ of the sense amplifier, yet relatively high in comparison to the impedance of tissue and body fluids. With no limitation intended, the ohmic value of the elements $R_1$ and $R_2$ may be in the range of from about three percent to ten percent of the input impedance of the sense amplifier and may be in the range of from 10 to 200 times greater than the impedance offered by tissue and body fluids. In implementing the invention, a sense amplifier having an input impedance of approximately one megohm has been employed with the impedance elements $R_1$ and $R_2$ being each 50 kohms. The typical impedance exhibited between the tip electrode 30 and the ring electrode 38 on a bipolar lead where the distal end thereof is disposed proximate the apex of the ventricle is in the order of 500 to 2,000 ohms.

OPERATION

As was pointed out above, adaptive sensing permits a pacemaker, without the need for any internal changes, to sense R-wave activity in a unipolar mode with a unipolar lead, and in a bipolar mode with a bipolar lead. In each instance, in accordance with this invention, the pacing function would be unipolar irrespective of the lead type employed. That is to say, when applying a stimulating impulse to the heart via the tip electrode 30, the return for that signal is via the body and the indifferent electrode.

Figure 3:
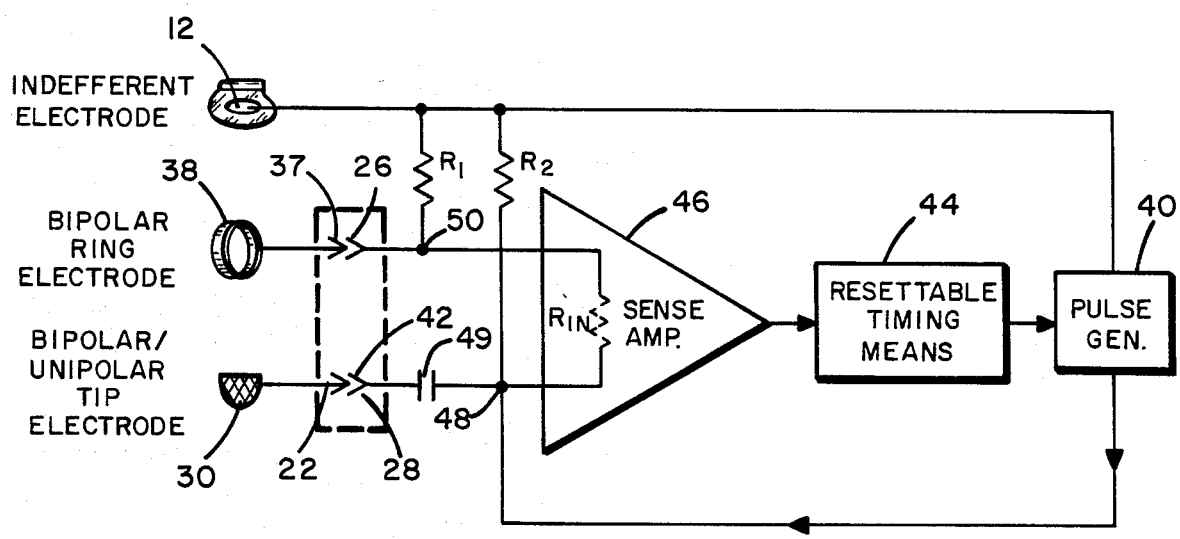
FIG. 3 is an electrical schematic diagram of an organ stimulator embodying the adaptive sensing circuit of the present invention.

With reference to FIG. 3, if there is no ring connected, i.e., a unipolar lead is inserted in the female receptacle of the pacemaker, the input to terminal 50 of the sense amplifier is controlled by the indifferent electrode through impedance element $R_1$ while the input to terminal 48 of the sense amplifier is controlled by the tip electrode 30. If a ring is connected, as is the case when a bipolar lead is used with the pacer, the input to terminal 48 is still controlled by the tip electrode 30, but the input to terminal 50 is largely controlled by the ring 38 instead of the indifferent electrode 12, since the tissue-to-ring impedance is much lower than the impedance of element $R_1$.

Studies made with a pacemaker configured as shown in the drawings hereof show that the system provides primarily unipolar sensing of R-wave activity when the ring electrode 38 is disconnected and primarily bipolar sensing when the ring 38 is connected. During these actual tests, output measurements were taken differentially from the indifferent electrode 12 to the ring electrode 38, from the indifferent electrode 12 to the tip electrode 30 and from the ring electrode 38 to the tip electrode 30. When these signals were compared to the signal that the pacemaker sense amplifier 46 would see, it was found that the latter signal strongly resembled the indifferent-to-tip signal when the ring was disconnected but resembled the ring-to-tip signal when the ring was connected. Only a slight attenuation in the unipolar signal was noted, and this is attributed to the voltage division produced by the impedance element $R_1$ in combination with $R_{in}$.

Thus, it can be seen that the present invention provides the design of a demand-type cardiac pacemaker whose sensing circuitry is capable of working with both bipolar or unipolar-style pacing/sensing leads without requiring any actions on the part of the physician to achieve this result.

The present invention has been described herein in considerable detail, in order to comply with the Patent Statutes, and to provide those skilled in the art with information needed to apply the novel principles, and to construct and use such specialized components as are required. However, it is to be understood that the invention can be carried out by specifically different equipment and devices, and that various modifications, both as to equipment details and operating procedures can be effected without departing from the scope of the invention itself.

What is claimed is:

1. In a cardiac pacer system of the type having electrical lead means comprising one or more distally disposed electrodes coupled by one or more elongated conductors to spaced and electrically isolated contact areas on a proximal connector pin, an implantable pulse generator means, resettable timing means coupled to said pulse generator means for causing said pulse generator means to produce electrical stimulating pulses at predetermined intervals unless said timing means is reset prior to the end of said predetermined intervals, sensing means coupled to said resettable timing means, said pulse generator means, said resettable timing means and said sensing means being housed in a moisture-proof container made at least in part from a conductive material which, when said housing is implanted in a living body, is in contact with tissue and body fluids, said container having terminal means for receiving said proximal connector pin, said terminal means having first and second spaced contacts for conductively engaging said spaced and electrically isolated contact areas on said proximal connector pin, an improved sensing means comprising:

(a) a sense amplifier exhibiting a predetermined input impedance characteristic between a pair of input terminals thereof, said sense amplifier having an output terminal coupled to said resettable timing means;

(b) first and second impedance elements, each of an impedance value which is at least ten times greater than the impedance of animal tissue and body fluids proximate the location of said distally disposed electrodes but less than ten percent of said predetermined input impedance of said sensing amplifiers;

(c) means coupling said first and second impedance elements between said conductive material of said housing and a first and a second of said pair of input terminals of said sense amplifier, respectively;

(d) means coupling said first spaced contact of said terminal means of said container to said first input terminal of said pair of input terminals of said sense amplifier means; and (e) means coupling said second spaced contact of said terminal means of said container to said second input terminal of said pair of input terminals of said sense amplifier means, said first and second spaced contacts in said terminal means of said container mating with said spaced and electrically isolated contact areas on said connector pin of said lead means.

2. The improved sensing means as in claim 1 wherein said electrical lead means is a unipolar lead with one distally disposed electrode coupled by one elongated conductor to one of said contact areas on said connector pin, said one contact area on said connector pin mating with said second spaced contact of said terminal means of said container.

3. The improved sensing means as in claim 1 wherein said electrical lead means is a bipolar lead with at least two distally disposed electrodes coupled by two separate eleongated conductors to at least two of said spaced and electrically isolated contact areas on said connector pin, said two contact areas on said connector pin mating with said first and second spaced contacts of said terminal means of said container.

4. The improved sensing means as in claim 1 wherein said first and second impedance elements are of a value in the range of from about three percent to ten percent of said predetermined input impedance characteristic of said sense amplifier and about 10 to 200 times greater than said impedance of said animal tissue and body fluids.

* * * * *